United States Patent [19]
Hoshowski

[11] Patent Number: 6,048,520
[45] Date of Patent: Apr. 11, 2000

[54] CLEAR LEAVE-ON HAIR TREATMENT COMPOSITION AND METHOD

[75] Inventor: Myra Ann Hoshowski, Addison, Ill.

[73] Assignee: Helene Curtis, Inc., Chicago, Ill.

[21] Appl. No.: 08/105,008

[22] Filed: Aug. 11, 1993

Related U.S. Application Data

[63] Continuation-in-part of application No. 07/950,825, Sep. 24, 1992, abandoned.

[51] Int. Cl.⁷ .............................. A61K 7/075; A61K 7/11
[52] U.S. Cl. ................ 424/70.17; 424/70.1; 424/70.122; 424/70.14; 424/70.15; 424/70.16; 424/70.28; 424/70.19
[58] Field of Search ........................... 424/401, 70, 70.1, 424/70.12, 70.122, 70.14–70.19, 70.28; 8/405

[56] References Cited

U.S. PATENT DOCUMENTS

| | | | |
|---|---|---|---|
| 3,939,095 | 2/1976 | Slinka | 252/316 |
| 4,126,674 | 11/1978 | Mausner | 424/31 |
| 4,885,159 | 12/1989 | Miyake | 424/450 |
| 5,021,200 | 6/1991 | Vanbergerghe et al. | 424/450 |
| 5,082,661 | 1/1992 | Melnik et al. | 424/401 |
| 5,089,269 | 2/1992 | Noda et al. | 424/456 |
| 5,234,711 | 8/1993 | Kamen | 427/213.34 |

FOREIGN PATENT DOCUMENTS 0261754  9/1991  European Pat. Off.  ......... A61K 7/50

*Primary Examiner*—Thurman K. Page
*Attorney, Agent, or Firm*—Milton L. Honig

[57] ABSTRACT

A transparent leave-on hair treatment composition including capsules of a water insoluble hair-treating compound encased in a shell material, such as gelatin or acacia gum. The aqueous leave-on composition is applied to the hair and the water insoluble hair-treating compound is released from the capsules to treat the hair. The shell disintegrates into sufficiently small residual particles such that the physical and esthetic properties of the hair, like shine and combability, are retained.

35 Claims, No Drawings

CLEAR LEAVE-ON HAIR TREATMENT COMPOSITION AND METHOD

CROSS REFERENCE TO RELATED APPLICATION

This is a continuation-in-part of U.S. application Ser. No. 07/950,825 filed Sep. 24, 1992 and now abandoned.

FIELD OF THE INVENTION

The present invention relates to a clear, or transparent, leave-on hair treatment composition including an encapsulated water insoluble hair-treating compound. The water insoluble hair-treating compound is encapsulated in a shell material, such as gelatin or acacia gum. The capsules including the water insoluble hair-treating compound are suspended in an aqueous carrier, and the resulting composition is applied to the hair. During or after application of the composition to the hair, the capsules are ruptured to release the water insoluble hair-treating compound. The clear composition is a leave-on composition and therefore is not rinsed from the hair. The shell of the capsule disintegrates into sufficiently small fragments such that the residual shell particles are not visible on the hair, and do not adversely affect the physical and esthetic properties of the hair, like shine and combability.

BACKGROUND OF THE INVENTION

Individuals buy and use a hair shampoo for its cleansing properties. Hair shampoos generally are formulated with highly effective synthetic surfactants, like anionic surfactants, to thoroughly clean the hair. Shampoos usually neither aid in detangling wet hair; nor impart any residual conditioning benefits to dry hair, such as manageability or styleability of hair sets; nor impart any other desired physical or esthetic properties to the hair.

Consequently, shampooed hair normally is left in a cosmetically-unsatisfactory state after washing with an anionic surfactant-based hair shampoo. Anionic surfactants not only remove the dirt and soil from the hair, but also remove essentially all of the sebum naturally present on the surface of the hair fibers. Therefore, the desirable properties of anionic surfactants that effectively clean the hair also serve to leave the hair in a cosmetically-unsatisfactory condition. In general, hair shampoo compositions containing anionic surfactants, or nonionic surfactants or amphoteric surfactants, leave the hair with an undesirable harsh, dull and dry touch, or feel, usually called "creak", after the hair is shampooed and then rinsed with water.

Furthermore, thoroughly cleansed hair also is extremely difficult to comb, in either the wet or dry state, because the individual hair fibers tend to snarl, kink, and interlock with each other. In addition, incompletely dried hair, such as hair dried with a towel, has poor brushing properties. Furthermore, the combing or brushing property of the hair remains poor, and the hair has undesirable electrostatic properties in a low humidity atmosphere that causes the hair to "fly away", thereby further reducing the brushing properties of the hair. The unsatisfactory combing or brushing property of hair immediately after shampooing, or during trimming treatments after shampooing, also causes hair damage, such as split ends or hair breakage. In addition, the natural luster and resiliency of the hair is reduced. Consequently, the overall unsatisfactory condition of the shampooed hair usually necessitates a subsequent post-shampoo treatment of the hair with a special conditioning composition to improve these undesirable physical characteristics. These conditioning compositions normally are applied separately from the hair shampoo, and usually are rinses, or cream-like emulsions or lotions.

Therefore, consumer needs traditionally have been met by the application of a shampoo to cleanse the hair, followed by the application of a conditioner composition to improve wet combing. The commonly accepted method has been to shampoo the hair, followed by rinsing the hair, and then separately applying a conditioner composition. The conditioner composition either is allowed to remain on the hair after application (leave-on composition), or is rinsed from the hair after application (rinse-off application). The leave-on hair conditioner composition often are gel materials of relatively high viscosity. As previously discussed, freshly shampooed hair is inclined to knot and tangle, and therefore is difficult to comb and difficult to manage. The combing problem has been solved by treating shampooed hair with a conditioner composition that coats the hair shaft and causes the individual hair shafts in a tress to resist tangling and matting because of the conditioner residue retained on the shaft.

In addition to conditioning the hair, consumers often desire to treat the hair with other types of hair treating compositions, such as, for example, a protection gel including a sunscreen or a hair gel including dyes to temporarily or semipermanently color the hair. The above-described hair conditioners, protection gels, hair fixatives and colorant hair gels often are applied as a leave-on composition, wherein the consumer applies the composition to the hair with the fingertips and does not subsequently rinse the composition from the hair.

The hair treatment compositions described above often include a water insoluble hair-treating compound to treat the hair, such as a silicone conditioning compound or a semi-permanent dye. However, such water insoluble hair-treating compounds are difficult to incorporate into an aqueous composition. One well-known method of incorporating the water-insoluble compound into the composition is to provide an opaque, emulsified composition. However, consumers often desire a transparent composition, primarily for esthetic reasons.

It is difficult however to incorporate a water insoluble compound into an aqueous composition and to retain both visual clarity and product performance, such as sufficient hair conditioning or protection of the hair from the sun. To achieve these goals, formulators have used encapsulated water insoluble compounds, and included the encapsulated compound in the hair treatment composition.

Encapsulation is the process wherein a water insoluble compound is encased in a shell material to provide a capsule of sufficiently small size such that the transparency of an aqueous composition is maintained. The encapsulated water insoluble compound does not contact the aqueous carrier, and composition transparency and performance are not reduced.

During or after application to the hair, the capsule is broken due to pressure, friction, or a similar physical process. The broken, or fractured, capsule releases the water insoluble hair-treating compound and the fractured shell particles cling to the hair. For a leave-on composition, the fractured shell particles are not rinsed from the hair. Therefore, a serious disadvantage demonstrated by leave-on compositions is the residual shell particles on the hair which are visible and decrease the shine of the hair, thereby adversely affecting the hair. Rinse-off compositions do not exhibit this disadvantage because the visible residual shell fragments are rinsed from the hair. Therefore, it would be advantageous to provide a leave-on encapsulated hair-treating composition that leaves the hair in an as good an esthetic condition as a rinse-off encapsulated hair-treating composition. Until the composition and method of the present invention, no such leave-on hair-treating composition has been available.

Prior patents have disclosed hair care compositions including encapsulated water insoluble compounds. For example, Mausner U.S. Pat. No. 4,126,174 discloses a shampoo-conditioner composition that simultaneously shampoos and conditions the hair. The composition includes a mineral oil conditioning agent encapsulated in gelatin. By definition, the shampoo-conditioners disclosed by Mausner must be rinsed from the hair. Therefore, the problem of residual shell fragments on the hair was neither considered nor addressed by Mausner because the disclosed composition, and the gelatin shell fragments, are rinsed from the hair. Mausner did not consider leave-on conditioning compositions, and did not teach that the disclosed rinse-off compositions could be used as a leave-on composition.

Only leave-on hair treatment compositions present the problem of large residual shell fragment particles remaining on the hair. Until the method of the present invention, no known investigator has studied the effects of residual shell fragments on the hair. Surprisingly and unexpectedly, it has been found that large residual shell fragments adversely affect hair properties.

Present day leave-on hair care compositions leave sufficiently large fractured shell particles on the hair such that the particles reflect light and therefore give the hair an unsightly and dull appearance. In addition, the large shell fragment particles catch on combs and reduce hair combability. Such adverse effects at least partially, and often significantly, offset the desired properties imparted to the hair by the water insoluble hair-treating compound, and thereby reduce composition effectiveness. In accordance with an important feature of the present invention, this previously unrecognized disadvantage in a leave-on composition that includes encapsulated compounds has been addressed and overcome.

Noda et al. U.S. Pat. No. 5,089,269 discloses cosmetic compositions comprising microcapsules including a hydrophobic component in a gelatin shell swollen with water. Noda et al. disclose several methods of manufacturing microcapsules having variable shell properties and core contents. Noda et al. teaches that a suitable mixture within the capsule reduces the undesirable feel of capsule fragments after breakage. Noda et al. do not teach rupture of the capsules into sufficiently small fragments that cannot be seen.

There is a significant difference between feeling a capsule shell fragment and seeing a capsule shell fragment. The encapsulated product can be formulated to overcome the gritty feel of capsule shell fragments, without addressing the presence of relatively large shell fragments that are visible. Therefore, encapsulated hair-treatment compositions can be formulated to rupture and to provide shell fragments that are visible on the hair but cannot be felt. The publication "Modern Cosmetic Liquids", R. Huttinger, Goldschmidt Chemical Co. 3/81. Nr. 55' English Ed., pp. 31–37, discloses that it is common to use a good spreading compound to overcome the gritty feel of shell fragments. Such a technique is used by Noda et al, wherein the encapsulated compound reduces the "feel" of gelatin shell material.

Other exemplary patents relating to hair treatment compositions including an encapsulated water insoluble compound are Melnik et al. U.S. Pat. No. 5,082,661 and Tanner European Patent Publication No. 0261754.

As will be demonstrated more fully hereinafter, a clear leave-on hair treatment composition of the present invention, comprising an aqueous suspension of transparent capsules including a water insoluble hair-treating compound encased in a shell material such as gelatin or acacia gum, effectively delivers the water insoluble hair-treating compound to the hair. Surprisingly and unexpectedly, the capsules, after rupture to release the water insoluble hair-treating compounds, disintegrate into sufficiently small fragments such that the residual shell fragment particles are not visible on the hair and do not adversely affect the physical or esthetic properties of the treated hair.

SUMMARY OF THE INVENTION

In brief, the present invention is directed to a method of treating the hair. More particularly, the present invention is directed to a method of treating the hair with a transparent, water-based composition including an encapsulated water insoluble hair-treating compound. The composition is not rinsed from the hair relatively soon after application, but is allowed to remain on the hair until at least the next shampooing.

During or after application of the composition to the hair, the water insoluble hair-treating compound is released from the capsules to treat the hair. The residual shell fragment particles of the capsule are sufficiently small such that the residual fragment particles are not visible on the hair and do not adversely affect the physical or esthetic properties of the treated hair.

Therefore, one aspect of the present invention is to provide a clear leave-on hair treatment composition comprising about 0.1% to about 10% by weight of capsules including a water insoluble hair-treating compound, wherein the capsules are suspended in an aqueous carrier.

Another aspect of the present invention is to provide a clear leave-on hair treatment composition wherein the capsules comprise a core material of a water insoluble hair-treating compound and a shell of a shell material, like gelatin or acacia gum.

Another aspect of the present invention is to provide a transparent leave-on hair treatment composition wherein the weight ratio of the core material to the shell material of the capsule is at least 95 to 5, on an anhydrous basis.

Yet another aspect of the present invention is to provide a clear leave-on hair treatment composition wherein the capsules break, or disintegrate, into residual shell fragment particles of about $10\mu$ (microns) or less in diameter.

Another aspect of the present invention is to provide a method of treating the hair with a clear leave-on hair treatment composition including capsules of a water insoluble hair-treating compound, wherein the composition delivers the water insoluble hair-treating compound to the hair, and wherein the physical and esthetic properties of the treated hair are not adversely affected by the residual shell fragment particles of the broken capsules.

These and other aspects and advantages of the present invention will become apparent from the following detailed description of the preferred embodiments.

DETAILED DESCRIPTION OF THE PREFERRED EMBODIMENTS

The clear leave-on hair treatment composition utilized in the method of the present invention comprises:

(a) a capsule, said capsule comprising:
  (i) a core of a water insoluble hair-treating compound, and
  (ii) a shell of a shell material that breaks, fragments, or disintegrates, into residual particles having a diameter of 10µ or less;
(b) a suspending agent to suspend the capsule; and
(c) a carrier comprising water.

The transparent leave-on composition is applied to, and remains on, the hair to treat the hair at least until the next shampooing. During or after application to the hair, the shell of the capsule breaks, or disintegrates, into sufficiently small fragments such that the physical and esthetic properties of the treated hair are not adversely affected.

The clear leave-on hair treatment composition includes about 0.1% to about 10% by weight of the capsules. In general, the capsules have a diameter of about 10 to about 3000µ. If desired to provide a particular esthetic effect, the capsules have a sufficiently large diameter such that the capsules are visible in the clear leave-on hair treatment composition. During application of the leave-on composition to the hair, the capsules are broken and the water insoluble hair-treating compound is released to contact and treat the hair. The water insoluble hair-treating compound is allowed to remain on the hair, and is not rinsed from the hair relatively soon after application. The shell of the capsule disintegrates into sufficiently small particle fragments such that the particle fragments are not visible and such that the physical and esthetic properties of the treated hair are not adversely affected by the presence of particle fragments on the hair.

The water insoluble hair-treating compound can be, for example, a conditioning agent, a hair protectant, a hair dye, or a mixture thereof. The term "water insoluble hair-treating compound" is defined as: 1) a water insoluble compound that 2) has a solubility in water of about 0.5 grams (g) or less per 100 milliliters (ml) of water, 3) has a refractive index of at least 1.3, 4) imparts a beneficial or desired property to the hair, and 5) can be encapsulated.

In a preferred embodiment, the water insoluble hair-treating compound present in the core of the capsule comprises at least about 95% by weight of the capsule, on an anhydrous basis. In one important embodiment of the present invention, the water insoluble hair-treating compound is a conditioning agent that imparts conditioning properties to the hair. In other important embodiments, the water insoluble hair-treating compound is a hair protectant or a hair dye.

Preferably, the water insoluble hair-treating compound is a liquid at room temperature. Alternatively, the water insoluble hair-treating compound is a solid that has been dissolved in a suitable water insoluble solvent, like silicone oil or mineral oil, to provide a liquid core for the capsule. The water insoluble solvent has a refractive index of at least 1.3 and a water solubility of about 0.5 g or less per 100 ml of water.

In the embodiment wherein the water insoluble hair-treating compound is conditioning agent, exemplary conditioning agents include, but are not limited to, a silicone conditioning agent, a hydrocarbon conditioning agent, a water insoluble fatty alcohol including about 12 to about 22 carbon atoms or a water insoluble fatty ester including about 9 to about 34 carbon atoms, the water-insoluble conditioning agents listed hereinafter, or mixtures thereof. Exemplary, but non-limiting, silicone conditioning agents include a polyalkyl siloxane. Mixtures of these silicone conditioning agents also can be used.

In one embodiment, the silicone conditioning agent is a nonvolatile silicone conditioning agent, like a polydimethylsiloxane compound, such as a mixture, in about a 2:1 weight ratio, of a low molecular weight polydimethylsiloxane fluid and a higher molecular weight polydimethylsiloxane gum. Preferred silicone gums include linear and branched polydimethylsiloxanes of the following general formula:

wherein n is a number from 2,000 to about 15,000, and preferably from about 2,000 to about 7,000. Silicone gums useful in compositions of the present invention are available from numerous commercial sources, including General Electric Company, Waterford, N.Y., and Dow Corning Corp., Midland, Mich.

The nonvolatile polydimethylsiloxane agent is included in an amount sufficient to impart improved combing and improved feel, such as softness, to the hair. As referred to herein, the nonvolatile polydimethylsiloxane compounds are nonfunctional siloxanes having a viscosity of from about 5 to about 600,000 cs (centistoke), and preferably from about 350 to about 10,000 cs, at 25° C. The so-called "rigid silicones", as described in U.S. Pat. No. 4,902,499, incorporated herein by reference, having a viscosity above 600,000 cs at 20° C., e.g., 700,000 cs plus, and a weight average molecular weight of at least about 500,000 also are useful in accordance with the present invention.

In another embodiment, a volatile silicone conditioning agent is used in the leave-on composition of the present invention as the water insoluble hair-treating compound, either alone or in conjunction with other water insoluble hair-treating compounds. The volatile silicone normally is a low molecular weight polydimethylsiloxane, however a low molecular weight polydimethylsiloxane including phenyl substituents also is useful in the compositions of the present invention. Furthermore, the low molecular weight polydimethylsiloxane compound can be a linear or a cyclic polydimethylsiloxane compound. The volatile polydimethylsiloxane compound provides lubrication and imparts hair conditioning properties to hair, and has sufficient volatility to slowly volatilize from the hair such that a residual buildup of silicone compound is not present on dry hair.

An example of a linear, low molecular weight, volatile polydimethylsiloxane compound useful in the composition and method of the present invention is hexamethyldisiloxane, available commercially under the tradename DOW CORNING 200 FLUID, from Dow Corning Corp., Midland, Michigan. Hexamethyldisiloxane has a viscosity of 0.65 cs (centistokes), is highly volatile, is nongreasy, provides lubrication, and improves the overall combing properties of the hair. Other linear polydimethylsiloxanes, such as decamethyltetrasiloxane, having a boiling point of about 195° C. and a viscosity of 1.5 centistokes; octamethyltrisiloxane; and dodecamethylpentasiloxane, also are useful in the composition of the present invention.

In addition, the cyclic, low molecular weight, volatile polydimethylsiloxanes, having the Cosmetic, Toiletry and Fragrance Associate (CTFA) designation cyclomethicones, also are useful in the composition and method of the present invention. The cyclomethicones are low molecular weight, water insoluble cyclic compounds having an average of about 3 to about 6 -[O-Si(CH$_3$)$_2$]- repeating group units per molecule and boil at atmospheric pressure in a range of from about 150° C. to about 250° C. Suitable cyclomethicones are available commercially under the tradenames SILICONE SF-1173 (octamethylcyclotetrasiloxane) and SILICONE SF-1202 (decamethylcyclopentasiloxane) from General Electric, Waterford, New York, and SILICONE 334 FLUID and SILICONE 345 FLUID from Dow Corning Corporation, Midland, Mich., the tetramer being listed first in each instance. The volatile cyclic silicones can be used in combination with a linear volatile silicone, and the volatile silicone conditioner can be used in conjunction with the nonvolatile silicone conditioner.

In another embodiment, the water insoluble conditioning compound included in the composition of the present invention is a nonvolatile hydrocarbon, such as mineral oil. The nonvolatile hydrocarbons provide many of the same benefits as the silicone conditioning agents, and can be included in the composition in conjunction with a silicone conditioning agent.

In yet another embodiment, a volatile hydrocarbon conditioning compound is included in the composition as the water insoluble hair treating compound, either alone or in conjunction with other water insoluble hair treating compounds. The volatile hydrocarbon conditioner, such as a hydrocarbon including about 10 carbon atoms to about 26 carbon atoms, has sufficient volatility to slowly volatilize from the hair to preclude a residual buildup of hydrocarbon on dry hair. The volatile hydrocarbon provides essentially the same benefits as the volatile silicone, such as lubrication and hair conditioning.

The preferred volatile hydrocarbon compound is an aliphatic hydrocarbon including from about 12 to about 24 carbon atoms, and has a boiling point in the range of from about 100° C. to about 300° C. Exemplary volatile hydrocarbons are depicted in general structural formula (IV), wherein n ranges from 2 to 5.

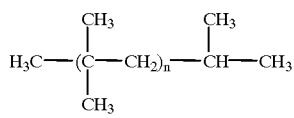

(IV)

Examples of volatile hydrocarbons useful in the compositions of the present invention are the commercially-available compounds PERMETHYL 99A and PERMETHYL 101A, corresponding to compound of general structural formula (IV) wherein n is 2 and 3, respectively, from Permethyl Corporation, Frazer, Pa. A volatile hydrocarbon compound is useful in the leave-on composition utilized in the present invention either alone, in combination with another volatile or nonvolatile hydrocarbon, or in combination with a volatile or nonvolatile silicone.

In another embodiment, the water insoluble conditioning compound is a fatty alcohol, wherein the fatty alcohol includes about 12 to about 22 carbon atoms. Preferably, the fatty alcohol is a liquid compound at room temperature. Exemplary fatty alcohols include, but are not limited to, lauryl alcohol, oleyl alcohol, myristyl alcohol, tallow alcohol, cetyl alcohol, stearyl alcohol, cetearyl alcohol, behenyl alcohol and combinations thereof. A fatty alcohol can be used alone, or in combination with a silicone conditioning agent or a hydrocarbon conditioning agent.

In another embodiment, the water insoluble conditioning compound is a fatty ester including about 9 to about 34 carbon atoms. Preferably, the fatty ester is a liquid compound at room temperature. The fatty component of the fatty ester can be derived from a fatty acid or a fatty alcohol, or a combination thereof. In addition, the fatty ester can be a straight chain fatty ester, like isopropyl myristate; a branched chain fatty ester, like Purcellin Oil; a benzoate ester, like $C_{12-15}$ alcohols benzoate; or a combination thereof.

For example, a useful class of fatty esters is derived from carboxylic acids having about 6 to about 12 carbon atoms, including both branched and straight chain carboxylic acids. In general, the $C_6$ to $C_{12}$ carboxylic acid is esterified with a fatty alcohol including about 12 to about 22 carbon atoms to provide a fatty ($C_{12}$ to $C_{22}$) ester of a $C_6$ to $C_{12}$ carboxylic acid that is useful in the present invention. Such fatty alcohols include, but are not limited to, lauryl alcohol, myristyl alcohol, cetyl alcohol, cetearyl alcohol, stearyl alcohol, isostearyl alcohol, oleyl alcohol, tallow alcohol, behenyl alcohol and mixtures thereof. Accordingly, fatty ($C_{12}$ to $C_{22}$) esters of $C_6$ to $C_{12}$ carboxylic acids useful in the composition and method of the present invention include, but are not limited to, cetyl octanoate, stearyl heptanoate, stearyl caprylate, stearyl octanoate, lauryl octanoate, myristyl heptanoate, and oleyl octanoate, or mixtures thereof. These fatty esters can occur naturally or can be synthesized.

In place of, or in combination with, the fatty ($C_{12}$ to $C_{22}$) ester of a $C_6$ to $C_{12}$ carboxylic acid, a fatty ester derived from a fatty acid including about 8 to about 22 carbon atoms esterified with an alcohol including 1 to about 6 carbon atoms can be included in the composition of the present invention. Examples of such fatty esters include, but are not limited to, isopropyl myristate, isopropyl palmitate, isopropyl laurate, isopropyl linoleate, isopropyl tallowate, isopropyl ricinoleate, methyl laurate, methyl linoleate, methyl myristate, methyl stearate, methyl ricinoleate, methyl caprylate, methyl oleate, methyl palmitate, methyl stearate, methyl behenate, methyl soyate, methyl tallowate, isopropyl behenate, isopropyl soyate, propyl oleate, butyl oleate, butyl stearate, methyl coconate, methyl lardate, isobutyl palmitate, butyl myristate, ethyl palmitate, ethyl myristate, ethyl oleate, ethyl stearate, isobutyl stearate, isobutyl myristate and combinations thereof.

Another class of fatty esters that can be included in the composition of the present invention, either alone or in combination with the fatty esters described above, is the benzoate esters. Suitable benzoate esters include esters of benzoic acid wherein the esterifying alcohol includes about 8 carbon atoms to about 22 carbon atoms. Examples of suitable benzoate esters include, but are not limited to, the commercial products FINSOLV TN, benzoic acid esterified with fatty alcohols including about 12 to about 15 carbon atoms; FINSOLV SB, isostearyl benzoate; FINSOLV P, PPG-15 stearyl ether benzoate; or combinations thereof, all available from Finetex Inc., Elmwood Park, N.J.

Examples of other specific water insoluble conditioning agents that can be incorporated into the conditioning shampoos of the present invention include, but are not limited to, polysiloxane polyether copolymers; acetylated lanolin alcohols; lanolin-derived extract of sterols and sterol esters; lanolin alcohol concentrate; isopropyl ester of lanolin fatty acids; polyol fatty acid; keratin protein derivatives; amino-functional silicones; fatty alcohol fraction of lanolin; mineral oil and lanolin alcohol mixture; high molecular weight esters of lanolin; 5 mole ethylene oxide adduct of soya sterol; stearic acid ester of ethoxylated methyl glucoside; hydroxylated lanolin; mixed ethoxylated and propoxylated long chain alcohols; hydrolyzed animal keratin; ethyl hydrolyzed animal keratin; avocado oil; sweet almond oil; grape seed oil; jojoba oil; apricot kernel oil; sesame oil; hybrid safflower oil; wheat germ oil; ethyl esters of hydrolyzed animal protein; blend of cetyl and stearyl alcohols with ethoxylated cetyl or stearyl alcohols; propoxylated (1–10 moles) lanolin alcohols; isostearamide DEA; and hydrolyzed collagen protein; and mixtures thereof. Other water insoluble conditioning agents are listed in *CTFA Cosmetic Ingredient Handbook, First Edition*, The Cosmetic Toiletry and Fragrance Association, Inc., New York, N.Y. (1988), pp. 71–73, hereby incorporated by reference.

Any of the above-listed conditioning agents that is solid at room temperature first is dissolved in a suitable solvent, like silicone oil, mineral oil, or other water insoluble solvent, that does not adversely affect the hair. The solubilized conditioning agent then is encapsulated.

In another embodiment, the water insoluble hair-treating compound is a hair protectant, like an ultraviolet absorber to protect hair from the effects of sunlight. Exemplary hair protectants include, but are not limited to, menthyl anthranilate, octyl salicylate, glyceryl PABA, octyl methoxycinnamate, octyl dimethyl PABA, and other hair protectants identified in the *CTFA Cosmetic Handbook*, pages 86–87. Similarly, in another embodiment, the water insoluble hair-treating compound is a water insoluble hair dye, like D & C Violet 2, Disperse Black 9, Disperse Blue 1, Solvent Red 24, Pigment Yellow 1, and other dyes identified in the *CTFA Cosmetic Handbook*, pages 70–71, or a mixture thereof, that imparts a temporary or semipermanent color to treated hair. A solid hair protectant or a solid hair dye is solubilized in a suitable solvent prior to encapsulating the hair protectant or hair dye in a shell. A combination of a water insoluble hair conditioning agent and/or hair protectant and/or a hair dye can be included in the liquid core of the capsule.

The capsule also includes a shell comprising a shell material that encapsulates the water insoluble hair-treating compound. In a preferred embodiment, the shell comprises 5% or less, by weight, of the capsules. Capsules including 5% or less, by weight, of shell material more easily fragment into sufficiently small shell fragment particles such that desirable hair properties are not adversely affected.

The shell material of the capsule is selected from a variety of compounds known to those skilled in the art. The selection of a particular shell material varies with the identity of the water insoluble hair-treating compound, and with the particular method utilized to manufacture the capsules. However, in every case, regardless of the material comprising the shell, or of the method of manufacturing the capsule, the shell of the capsule is designed such that the shell disintegrates into particles having a diameter of about $10\mu$ or less. Fragment particles greater than about $10\mu$ in diameter are visible on the hair and can reflect light, thereby causing a dull appearance of the hair.

The material comprising the shell of the capsules can be a natural, a synthetic or a semisynthetic material. Exemplary materials comprising the shell of the capsule include but are not limited to gum acacia (gum arabic), agar, agarose, a maltodextrin, sodium alginate, calcium alginate, dextran, a fat, a fatty acid, cetyl alcohol, milk solids, molasses, gelatin, gluten, albumin, shellac, starch, a caseinate, a stearin, sucrose, a wax (e.g., beeswax, carnauba, and spermaceti), cellulose acetate, cellulose acetate butyrate, cellulose acetate phthalate, cellulose nitrate, ethylcellulose, hydroxypropylcellulose, hydroxypropylmethylcellulose, hydroxypropylmethylcellulose phthalate, methyl cellulose, sodium carboxymethylcellulose, hydrogenated tallow, myristyl alcohol, glycerol monopalmitate, glycerol dipalmitate, hydrogenated castor oil, glycerol monostearate, glycerol distearate, glycerol tristearate, 12-hydroxystearyl alcohol, an acrylic polymer or copolymer [e.g., polyacrylamide, poly(alkyl cyanoacrylate), and poly(ethylene-vinyl acetate)], aluminum monostearate, a carboxyvinyl polymer (CARBOPOL), a polyamide, poly(methyl vinyl ether-maleic anhydride), poly(adipyl-L-lysine), a polycarbonate, polyterephthalamide, polyvinyl acetate phthalate, poly (terephthaloyl-L-lysine), a polyarylsulfone, poly (methylmethacrylate), poly($\epsilon$-caprolactone), polyvinylpyrrolidone, polydimethylsiloxane, polyoxyethylene, a polyester, polyglycolic acid, polylactic acid, polyglutamic acid, polylysine, polystyrene, poly (styrene-acrylonitrile), a polyimide, poly(vinyl alcohol), and mixtures thereof. A preferred shell material is gelatin or acacia gum.

Typically, a crosslinking agent, like glutaraldehyde or formaldehyde, is included in the shell to help form a self-sustaining capsule. Other useful crosslinking agents include alum, copper sulfate, tannic acid and gallic acid. The selection of a particular crosslinking agent can effect the properties of the shell. For example, formaldehyde provides a more elastic shell and tannic acid provides a more brittle shell.

The capsules are prepared by methods well known in the art, such as coacervation, interfacial polymerization, spray drying, centrifugal extrusion and electrostatic deposition. For each method, the particular manufacturing variables are controlled to provide capsules: 1) having a diameter of about 10 to about $3000\mu$; 2) having a shell that disintegrates into provide capsules: 1) having a diameter of about 10 to about $3000\mu$; 2) having a shell that disintegrates into residual particles of about 5 to about $10\mu$ in diameter; and 3) preferably, but not necessarily, having a ratio of core material to shell material of at least about 95 to 5, on an anhydrous basis.

Those skilled in the art are able to select and adjust manufacturing variables to provide a capsule having the above-identified properties. The shell therefore can be made pliable or rigid, or fragile or strong. The shell strength can be controlled by a judicious selection of shell thickness, shell material, shell additives, and after-treatment of the shell (either physical or chemical). For example, in a coacervation process that provides a capsule having a gelatin shell encapsulating a silicone conditioning agent, suitable adjustment of pH and agitation helps provide a capsule having a shell that disintegrates into shell fragments of about $10\mu$ or less.

A skilled artisan likewise can manipulate the identity of shell material and the manufacturing variables, like temperature, pH, shell thickness and agitation speed, to encapsulate other core materials in a capsule having a sufficient elasticity or rigidity and fragileness or toughness, to disintegrate into shell fragment particles of about $10\mu$ or less in diameter. Noda et al. U.S. Pat. No. 5,089,269, incorporated herein by reference, discloses various methods of manufacturing microcapsules that disintegrate into small shell fragment particles.

In addition to the capsule, the aqueous leave-on hair treatment composition also includes a suspending agent to suspend the capsules in the aqueous carrier. Essentially any suspending agent can be utilized, provided that the suspending agent suspends capsules having a diameter of about 10 to about $3000\mu$, and provided that the suspending agent provides a clear composition. The suspending agent homogeneously disperses the capsules throughout the leave-on composition for at least the expected life of the product, and does not adversely affect the ability of the composition to treat the hair.

Therefore, useful suspending agents include, but are not limited to, carrageenan, polyacrylic acid, polyacrylate salts, ethylene/vinyl acetate copolymers, maltodextrin, polyvinyl alcohol, xanthan gum, nitrocellulose, polyethylenimine, polyethylacrylate, guar gum, karaya gum, polyvinylpyrrolidone, and mixtures thereof. Numerous other well-known suspending agents are listed in the *CTFA Cosmetic Ingredient Handbook, First Edition,* The Cosmetic, Toiletry and Fragrance Association (1988), pp. 97–100, hereby incorporated by reference. The suspending agent is included in the clear leave-on hair treatment composition in an amount of about 0.1 to about 1% by weight of the composition. Preferably, the suspending agent is present in an amount of about 0.2% to about 0.8% by weight of the composition.

In addition to the above-described ingredients, other common cosmetic components and additives can be included in the leave-on hair treatment composition of the present invention to impart desirable functional or esthetic properties, as long as the basic properties of the composition are not adversely affected. Such optional cosmetic components and additives include, but are not limited to, nonionic surfactants, cationic surfactants, amphoteric surfactants, fragrances, dyes, hair colorants, inorganic salts, humectants, hydrotropes, solubilizers, preservatives, water softening agents, buffers and the like. Each of these optional components and additives usually are present in weight percentages of 0% up to about 5% by weight of the leave-on composition, and usually 0% to about 20% by weight of the leave-on composition in total.

If a dye is incorporated into the leave-on composition, the dye preferably is included in the core material of the capsule or in the aqueous carrier, as opposed to the shell material of the capsule. If a sufficient amount of a dye is present in the material comprising the shell of the capsule, then the capsule may disintegrate into fragment particles having a diameter greater than $10\mu$ and adversely affect the hair.

The carrier of the leave-on hair treatment composition is predominantly water, but nonaqueous solvents also can be included to help solubilize composition ingredients that are not sufficiently soluble in water, to adjust the viscosity of the composition, or to act as a humectant. Suitable solvents include polyols, like glycerol; glycols, like ethylene glycol, propylene glycol and hexylene glycol; or mixtures thereof. The optional nonaqueous solvents should not adversely affect the ability of the composition to treat the hair and scalp, or adversely affect consumer appeal of the composition. A nonaqueous solvent can be present in a composition of the present invention in an amount ranging from 0% up to about 5% by weight of the composition.

To achieve the full advantage of the present invention, the leave-on hair treatment composition is a viscous mixture, like a gel, having a viscosity in the range of about 50,000 cps (centipoises) to about 100,000 cps, that is stable indefinitely at temperatures normally found in commercial product storage and shipping. A composition of the present invention generally is a suspension that is stable and that resists phase separation or settling of composition ingredients at a temperature of about 20° C. to about 25° C. essentially indefinitely. Preferably, the composition includes visible capsules that fracture during or after application to the hair. The compositions also have demonstrated sufficient stability to phase separation and settling of ingredients at temperatures normally found in commercial product storage and shipping to remain unaffected for periods of one year or more.

In accordance with the method of the present invention, leave-on hair treatment compositions were prepared, then applied to human hair. The capsules present in the leave-on hair treatment composition are broken by fingertip pressure during application of the composition to the hair and by the pressure and friction associated with combing the composition throughout the hair. The leave-on composition generally is allowed to remain on the hair until the next shampooing. The following compositions of Examples 1 through 4 demonstrate that capsules which disintegrate into residual shell fragment particles of about $10\mu$ or less in diameter provide shinier hair that is easier to comb.

To demonstrate the new and unexpected results achieved by the method of the present invention, the following Example 1 was prepared by first dispersing the suspending agent in water. The aqueous suspension of the suspending agent then was solubilized by adding the triethanolamine. The remaining composition ingredients then were added to the resulting mixture individually, in any desired order. Finally, the capsules were added to the composition with gentle mixing to uniformly disperse the capsules throughout the composition. The capsules were manufactured by standard coacervation processes wherein the temperature, pH, ratio of core material to shell material, agitation and other manufacturing parameters were varied to provide capsules with shells having a variable elasticity and strength.

EXAMPLE 1

Clear Styling Gel Including Encapsulated Silicone Conditioning Agent

| Ingredient | % by weight [1] |
| --- | --- |
| Suspending Agent [2] | 0.40 |
| Triethanolamine [3] | 0.55 |
| Tetrasodium EDTA [4] | 0.04 |
| PVP/VA Copolymer [5] | 4.10 |
| Surfactant [6] | 0.10 |
| Fragrance | 0.05 |
| Preservative [7] | 0.45 |
| Capsules [8] | 1.75 |
| Soft Water | q.s. to 100% |

[1] Percent by weight of active ingredient in the composition;
[2] CARBOPOL 940, crosslinked polyacrylic acid, available from B. F. Goodrich Chemical Co., Cleveland, Ohio;
[3] Solubilizing agent for CARBOPOL 940;
[4] Added as a 39% aqueous solution of tetrasodium ethylenediaminetetraacetate;
[5] Styling resin for the hair;
[6] Nonoxynol 10 to solubilize the fragrance;
[7] Diazolidinyl Urea, DMDM hydantoin and methylchloroisothiazolinone; and
[8] ARCAPSULE MP912, encapsulated dimethicone (i.e., polydimethylsiloxane), available from Arcade Inc., Chattanooga, TN.

The composition of Example 1 (one gram) was applied to clean, dry, naturally dark brown tresses of normal virgin human hair, each weighing four grams, and available from DeMeo Brothers, New York, N.Y. Accordingly, seven dimethicone capsules, having a gelatin shell and a ratio of dimethicone (core) to gelatin (shell) of 95.4 to 4.6, were applied to each hair tress. Each hair stress was gently stroked ten times using a thumb and index finger to apply the composition of Example 1 to the tress and release the dimethicone core of the capsule. The composition of Example 1 was not rinsed from the treated hair tress.

Each treated hair tress then was visually inspected. No residual shell fragment particles were observed. The hair tresses were shiny, having no dull areas, and were easy to comb. A photomicrograph of the treated hair tresses, which magnified the hair tress 20× (times), failed to expose any residual shell fragment particles, thereby demonstrating that the shell fragment particles on the treated hair tress had a diameter of about $10\mu$ or less.

A comparative composition also was prepared. The comparative composition was identical to the composition of Example 1 except the capsules had a ratio of core material to shell material of 93.3 to 6.7. The composition of Example 1 and the comparative composition each included capsules having an average size of 1800μ, which is a typical average capsule size for a rinse-off encapsulated composition. The comparative composition also was applied to clean, brown hair tresses in an identical manner to the composition of Example 1. An examination of the tresses treated with the comparative composition showed that the gel was uniformly applied to the tresses, but that large shell fragment particles were present on the hair. The hair tresses also appeared dull in areas where the large shell fragments were present.

The appearance of the hair treated with the composition of Example 1 is very different from the appearance of the hair treated with the comparative composition. The capsules of the comparative composition disintegrated into fragments of about 80 to about 900 microns in diameter. The capsules of the composition of Example 1 disintegrated into fragments of 10 microns or less in diameter. The large residual fragments of the comparative composition are visible on the hair, catch on combs thereby decreasing combability of the hair, cause "dandruff" flakes, reduce the shine of the hair, and generally adversely affect the esthetic properties of the treated hair. The conditioning agent (i.e., dimethicone) does not mitigate the effect of the particle size, thus it is the size of the residual shell fragment that determines whether a capsule is suitable for a leave-on composition. The large shell fragments of the comparative composition therefore are not a disadvantage in a rinse-off composition, but are a disadvantage in a leave-on composition.

Therefore, although the comparative composition imparted conditioning properties to treated hair tresses, the desired conditioning properties were partially offset by the presence of large shell fragments. The method of the present invention overcomes this disadvantage and allows a hair treatment composition to impart the full beneficial or desired properties to treated hair.

To further demonstrate the method of the present invention, the composition of Example 2 also was prepared and applied to human hair tresses.

EXAMPLE 2

Clear Styling Gel Including Encapsulated Silicone Conditioning Agent

| Ingredient | % by weight [1] |
| --- | --- |
| Suspending Agent [9] | 0.35 |
| Polyquaternium 4 [10] | 0.50 |
| Triethanolamine [3] | 0.55 |
| Tetrasodium EDTA [4] | 0.04 |
| PVP/Dimethylaminoethylmethacrylate Copolymer [11] | 5.00 |
| Sorbitol [12] | 0.35 |
| Acetamide MEA/Lactamide MEA [13] | 0.10 |
| Resin Modifier [14] | 0.50 |
| Preservative [7] | 0.40 |
| Surfactant [5] | 0.10 |
| Fragrance | 0.10 |
| Capsules [15] | 3.00 |
| Soft Water | q.s. to 100% |

[9] CARBOPOL 980, crosslinked polyacrylic acid, available from B. F. Goodrich Chemical Co., Cleveland, Ohio;
[10] Hair conditioning agent;
[11] Styling resin for the hair;
[12] Humectant;
[13] Hair conditioning agent;
[14] Dow Corning Q2-5220, a laurylmethicone copolyol, available from Dow Corning Corp., Midland, MI.; and,
[15] Dimethicone encapsulated in gelatin, average diameter 900 μ, available from Arcade Inc., Chattanooga, TN.

The composition of Example 2 was a clear pink gel having a viscosity of about 63,000 cps and a pH of about 6.9. The dimethicone capsules remained suspended in the composition after about one year storage. The composition of Example 2 was applied to human hair tresses in a manner identical to the composition of Example 1. The treated hair was shiny and easy to comb. Residual shell fragment particles were not observed in a visual inspection of the treated hair tresses, or in magnified photomicrographs of the treated hair tresses.

EXAMPLE 3

Clear Styling Gel Including Encapsulated Silicone Conditioning Agent

| Ingredient | % by weight [1] |
| --- | --- |
| Suspending Agent [9] | 0.36 |
| Polyquaternium 4 [10] | 0.45 |
| Triethanolamine [3] | 0.57 |
| Tetrasodium EDTA [4] | 0.10 |
| PVP/Dimethylaminoethylmethacrylate Copolymer [11] | 4.50 |
| Sorbitol [12] | 0.30 |
| Acetamide MEA/Lactamide MEA [13] | 0.10 |
| Resin Modifier [14] | 0.45 |
| Preservative [7] | 0.40 |
| Surfactant [5] | 0.21 |
| Fragrance | 0.07 |
| Capsules [16] | 1.50 |
| Soft Water | q.s. to 100% |

[16] Silicone Oil and an ester encapsulated in gelatin, capsule size range about 425 μ to about 2800 μ, available from LIPO Technologies, Inc., Dayton, Ohio.

The composition of Example 3 included a conditioning agent (i.e., a mixture of dimethicone and neopentyl glycol dicaprylate/dicaprate) which was different from the conditioning agent included in the compositions of Examples 1 and 2 and in the comparative example. The capsules in the composition of Example 3 range in size from about 425μ to about 2800μ. The composition of Example 3 was used in a half-head salon test.

In a half-head test, the composition of interest (the composition of Example 3) is applied to one side of a head of hair, and the product used for comparison (the composition of Example 1) is applied to the other side of the head. After the treatment, each side of hair is judged for a variety of hair conditioning properties by a trained judge on a ranking of 1 unit (worst) to 5 units (best). Five different heads of hair are so treated, and each head of hair is evaluated by a trained judge. Then ratings of the judges for each hair conditioning property are averaged, and a difference in rating one side of hair compared to the other side of hair of at least 0.3 units is considered a significant difference for that particular hair conditioning property.

The two treated one-half heads of hair were compared, subjectively, with respect to wet combing, wet feel, application pattern, evenness of application, ease of spreading, wet tack (on hands), ease of setting, pull of brush, crust, dry comb, dry feel, dry tack, coating, sheen/luster, pliability, volume, static, flaking/dust, curl retention and east of handling. Such parameters are standard in salon tests and are known to those skilled in the art.

There were no significant differences between hair treated with the composition of Example 1 and hair treated with the composition of Example 3, even though the conditioning agents and shell components of the two compositions differed. No differences were observed because the capsules in the compositions of Examples 1 and 3 disintegrated into residual particles of $10\mu$ or less in diameter. No residual shell fragments were visible on either one-half of treated hair. Accordingly, the important factor is the size of the residual shell particles as opposed to the identity of the water insoluble conditioning agent present in the capsule or to the identity of the components comprising the shell.

The composition of Example 4 includes capsules comprising a hair protectant encapsulated in a shell comprising gelatin and gum acacia.

EXAMPLE 4

Clear Gel Including Encapsulated Hair Protectant (Sunscreen)

| Ingredient | % by weight [1] |
|---|---|
| Suspending Agent [9] | 0.36 |
| Polyquaternium 4 [10] | 0.45 |
| Triethanolamine [3] | 0.57 |
| Tetrasodium EDTA [4] | 0.10 |
| PVP/Dimethylaminoethylmethacrylate Copolymer [11] | 4.50 |
| Sorbitol [12] | 0.50 |
| Acetamide MEA/Lactamide MEA [13] | 0.10 |
| Resin Modifier [14] | 0.45 |
| Preservative [7] | 0.40 |
| Surfactant [5] | 0.21 |
| Fragrance | 0.07 |
| Capsules [17] | 1.00 |
| Soft Water | q.s. to 100% |

[17] Octyl methoxycinnamate (a sunscreen hair protectant) encapsulated in gelatin and gum acacia, available from Hallcrest, Glenview, IL.

The composition of Example 4 includes capsules having a size of about $1200\mu$ to about $1500\mu$. The capsules encapsulated the hair protectant octyl methoxycinnamate. The composition of Example 4 was applied to human hair tresses in an identical manner described above for the composition of Example 1. The treated hair was not rinsed. After application, no residual shell fragments were visible (i.e., the residual shell fragments were less than $10\mu$ in diameter) and the treated hair was shiny and demonstrated excellent esthetic properties.

To further demonstrate the method of the present invention, hair tresses were treated with various compositions and examined for residual shell fragments and for acceptable esthetic properties. All treated hair samples were compared to an untreated, clean hair tress obtained from DeMeo Brothers, N.Y., N.Y. The untreated hair tress, denoted N1, was used as a control sample. All virgin hair tresses N1 through N7 were obtained from DeMeo Brothers, N.Y., N.Y.

Another hair tress was treated with a composition similar to the composition of Example 1 but which excluded the capsules. The composition was not rinsed from the tress. The treated tress (N2) was examined visually. Tress N2 was less shiny than, but otherwise identical in appearance to, control tress N1.

A third hair tress (N3) was treated with the composition of Example 1. Tress N3 was not rinsed after application of the composition of Example 1. Tress N3 was identical to tress N1 and shiner than tress N2 by visual inspection. Tress N3 was well conditioned and, like tresses N1 and N2, no residual shell fragments were visible on the hair. Tress N3 is an example of hair treated by the method of the present invention.

A fourth hair tress (N4) was treated with a composition having identical ingredients as Example 1, but wherein the capsules were replaced by capsules typically included in a rinse-off shampoo/bath product. Tress N4 was not rinsed, and was visually examined. Large visible shell fragments were present on the hair tress. Tress N4 was esthetically unsatisfactory and was unappealing because the presence of large flakes of residual shell material. Tress N4 is more difficult to comb than tresses N1 through N3.

A fifth hair tress (N5) was treated with a composition including a titanium dioxide ($TiO_2$) sunscreen ($200\mu$ $TiO_2$ particle size). A sixth hair tress (N6) was treated with a composition including titanium dioxide and iron oxide (45 to about $150\mu$ particle size). The hair tresses N5 and N6 were not rinsed. Tresses N5 and N6 were duller in appearance than tresses N1 through N3 by visual inspection. The titanium dioxide and iron oxide particles in tresses N5 and N6 could not be felt by rubbing the tresses between the fingertips. Tresses N5 and N6 therefore demonstrate that compositions which have a good feel, e.g., do not feel gritty, can nevertheless impart adverse visual properties to treated hair.

A seventh hair tress (N7) was treated with a commercial leave-on hair conditioner including capsules (FRIZZ EASE GEL available from John Freida Prof. Haircare, Inc., Wilton, Conn.). Tress N7 was examined visually, and large residual shell fragments were easily visible on the tress. Tress N7 was esthetically unsatisfactory because of the presence of visible "dandruff" like flakes of residual shell material on the treated hair.

Therefore, the method of the present invention provides treated hair having improved physical and esthetic properties. The clear leave-on hair treatment composition applied to the hair overcomes a distinct drawback in prior leave-on hair treatments that heretofore has not been addressed. The present method utilizes an encapsulated hair-treating compound wherein the capsule shell disintegrates into sufficiently small residual fragments such that the physical and esthetic properties of the treated hair are not adversely affected. Accordingly, the overall performance of the leave-on hair treatment composition is enhanced.

Obviously, many modifications and variations of the invention as hereinbefore set forth can be made without departing from the spirit and scope thereof, and therefore any such limitations should be imposed as are indicated by the appended claims.

What is claimed is:

1. A method of treating the hair comprising:
   (a) applying a sufficient amount of an aqueous, transparent, leave-on hair conditioning composition to hair to impart a physical or esthetic property to the hair, said leave-on hair conditioning composition comprising:
      (i) capsules having a diameter of about 425 to about 2800 microns, said capsules comprising:
         (A) a water insoluble conditioning compound encapsulated in
         (B) a shell material;
      (ii) a suspending agent to suspend the capsules; and
      (iii) a carrier comprising water;
   (b) breaking the capsules while the capsules are in contact with the hair to release the water insoluble conditioning compound;
   (c) while simultaneously disintegrating the shell material into residual particles having a diameter of about 10 microns or less; and
   (d) allowing the hair conditioning composition and the residual particles of shell material to remain in contact with the hair at least until the next hair shampooing.

2. The method of claim 1 wherein the leave-on composition includes about 0.1% to about 10% by weight of the capsules.

3. The method of claim 1 wherein the capsules are broken during application of the hair treatment composition to hair or by combing the hair after application of the hair treatment composition.

4. The method of claim 1 wherein the capsules comprise at least about 95% by weight of the water insoluble conditioning compound, on an anhydrous basis.

5. The method of claim 1 wherein the water insoluble conditioning compound has a refractive index of at least 1.3.

6. The method of claim 1 wherein the water insoluble conditioning compound is a liquid at room temperature.

7. The method of claim 1 wherein the water insoluble conditioning compound is a solid at room temperature and is solubilized in a water insoluble solvent.

8. The method of claim 1 wherein the conditioning compound is a silicone conditioning agent, a hydrocarbon conditioning agent, a water insoluble fatty alcohol including about 12 to about 22 carbon atoms, a water insoluble fatty ester including about 9 to about 34 carbon atoms, or mixtures thereof.

9. The method of claim 8 wherein the silicone conditioning agent is a nonvolatile silicone conditioning agent, a volatile silicone conditioning agent, or a mixture thereof.

10. The method of claim 8 wherein the hydrocarbon conditioning agent is a nonvolatile hydrocarbon conditioning agent, a volatile hydrocarbon conditioning agent, or a mixture thereof.

11. The method of claim 1 wherein the conditioning compound is selected from the group consisting of a polysiloxane polyether copolymer; an acetylated lanolin alcohol; a lanolin-derived extract of sterols and sterol esters; lanolin alcohol concentrate; an isopropyl ester of lanolin fatty acid; polyol fatty acid; a keratin protein derivative; an amino-functional silicone; fatty alcohol fraction of lanolin; a mineral oil and lanolin alcohol mixture; a high molecular weight ester of lanolin; 5 mole ethylene oxide adduct of soya sterol; stearic acid ester of ethoxylated methyl glucoside; hydroxylated lanolin; a mixed ethoxylated and propoxylated long chain alcohol; hydrolyzed animal keratin; ethyl hydrolyzed animal keratin; avocado oil; sweet almond oil; grape seed oil; jojoba oil; apricot kernel oil; sesame oil; hybrid safflower oil; wheat germ oil; an ethyl ester of hydrolyzed animal protein; a blend of cetearyl alcohol with an ethoxylated cetyl or stearyl alcohols; a propoxylated (1–10 moles) lanolin alcohol; isostearamide DEA; hydrolyzed collagen protein; and mixtures thereof.

12. The method of claim 1 wherein the shell material is selected from the group consisting of gelatin, gum acacia, agar, agarose, a maltodextrin, sodium alginate, calcium alginate, dextran, a fat, a fatty acid, cetyl alcohol, milk solids, molasses, gluten, albumin, shellac, starch, a caseinate, a stearin, sucrose, a wax, cellulose acetate, cellulose acetate butyrate, cellulose acetate phthalate, cellulose nitrate, ethylcellulose, hydroxypropylcellulose, hydroxypropylmethylcellulose, hydroxymethylcellulose phthalate, methyl cellulose, sodium carboxymethylcellulose, hydrogenated tallow, myristyl alcohol, glycerol monopalmitate, glycerol dipalmitate, hydrogenated castor oil, glycerol monostearate, glycerol distearate, glycerol tristearate, 12-hydroxystearyl alcohol, an acrylic polymer, an acrylic copolymer, aluminum monostearate, a carboxyvinyl polymer, a crosslinked polyacrylic acid, a polyamide, poly(methyl vinyl ether-maleic anhydride), poly(adipyl-L-lysine), a polycarbonate, polyterephthalamide, polyvinyl acetate phthalate, poly(terephthaloyl-L-lysine), a polyvinylsulfone, poly(methylmethacrylate), poly($\epsilon$-caprolactone), polyvinylpyrrolidone, polydimethylsiloxane, polyoxyethylene, a polyester, polyglycolic acid, polyacetic acid, polyglutamic acid, polylysine, polystyrene, poly(styrene-acrylonitrile), a polyimide, poly(vinyl alcohol), and mixtures thereof.

13. The method of claim 12 wherein the shell material further comprises a crosslinking agent.

14. The method of claim 1 wherein the leave-on composition includes about 0.1% to about 1% by weight of the suspending agent.

15. The method the group consisting of claim 1 wherein the suspending agent is selected from the group consisting of carrageenan, polyacrylic acid, a polyacrylate salt, an ethylene/vinyl acetate copolymer, a maltodextrin, polyvinyl alcohol, xanthan gum, nitrocellulose, polyethylenimine, polyethylacrylate, guar gum, karaya gum, polyvinylpyrrolidone, and mixtures thereof.

16. The method of claim 1 wherein the leave-on composition has a viscosity of about 50,000 to about 100,000 centipoises.

17. The method of claim 1 wherein the leave-on composition comprises:
   about 1% to about 8% by weight of the capsules, said capsules comprising:
      1) a water insoluble conditioning compound selected from a nonvolatile silicone conditioning agent, a volatile silicone conditioning agent, a nonvolatile hydrocarbon conditioning agent, a volatile hydrocarbon conditioning agent, and mixtures thereof, and
      2) a shell material selected from the group consisting of gelatin, acacia gum, and mixtures thereof; and
   about 0.2% to about 0.8% by weight of a crosslinked polyacrylic acid suspending agent.

18. A method of treating the hair comprising:
   (a) applying a sufficient amount of an aqueous, transparent, leave-on hair protectant composition to hair to impart a physical or esthetic property to the hair, said leave-on hair protectant composition comprising:
      (i) capsules having a diameter of about 425 to about 2800 microns, said capsules comprising:

(A) a water insoluble hair protectant compound encapsulated in
(B) a shell material;
(ii) a suspending agent to suspend the capsules; and
(iii) a carrier comprising water;
(b) breaking the capsules while the capsules are in contact with the hair to release the water insoluble hair protectant compound;
(c) while simultaneously disintegrating the shell material into residual particles having a diameter of about 10 microns or less; and
(d) allowing the hair protectant composition and residual particles of shell material to remain in contact with the hair at least until the next hair shampooing.

19. The method of claim 18 wherein the hair protectant has a refractive index of at least 1.3

20. The method of claim 18 wherein the hair protectant is selected from menthyl anthranilate, octyl salicylate, glyceryl PABA, octyl methoxycinnamate, octyl dimethyl PABA, and mixtures thereof.

21. The method of claim 18 wherein the leave-on composition includes about 0.1% to about 10% by weight of the capsules.

22. The method of claim 18 wherein the leave-on composition has a viscosity of about 50,000 to about 100,000 centipoises.

23. The method of claim 18 wherein the leave-on composition comprises:
about 1% to about 8% by weight of the capsules, said capsules comprising:
1) a water insoluble hair protectant compound, and
2) a shell material selected from the group consisting of gelatin, acacia gum, and a mixture thereof; and
about 0.2% to about 0.8% by weight of a crosslinked polyacrylic acid suspending agent.

24. The method of claim 18 wherein the capsules comprise at least about 95% by weight of the water insoluble protectant compound, on an anhydrous basis.

25. The method of claim 18 wherein the shell material further comprises a crosslinking agent.

26. The method of claim 18 wherein the leave-on composition includes about 0.1% to about 1% by weight of the suspending agent.

27. A method of treating the hair comprising:
(a) applying a sufficient amount of an aqueous, transparent, leave-on hair dye composition to hair to impart an esthetic property to the hair, said leave-on hair dye composition comprising:
(i) capsules having a diameter of about 425 to about 2800 microns, said capsules comprising:
(A) a water insoluble hair dye encapsulated in
(B) a shell material;
(ii) a suspending agent to suspend the capsules; and
(iii) a carrier comprising water;
(b) breaking the capsules while the capsules are in contact with the hair to release the water insoluble hair dye;
(c) while simultaneously disintegrating the shell material into residual particles having a diameter of about 10 microns or less; and
(d) allowing the hair dye composition and the residual particles of shell material to remain in contact with the hair at least until the next hair shampooing.

28. The method of claim 27 wherein the hair dye has a refractive index of at least 1.3.

29. The method of claim 27 wherein the hair dye is selected from the group consisting of D and C Violet 2, Disperse Black 9, Disperse Blue 1, Solvent Red 24, Pigment Yellow 1, and mixtures thereof.

30. The method of claim 27 wherein the leave-on composition includes about 0.1% to about 10% by weight of the capsules.

31. The method of claim 27 wherein the leave-on composition comprises:
about 1% to about 8% by weight of the capsules, said capsules comprising:
1) a water insoluble hair dye, and
2) a shell material selected from the group consisting of gelatin, acacia gum, and a mixture thereof; and
about 0.2% to about 0.8% by weight of a crosslinked polyacrylic acid suspending agent.

32. The method of claim 27 wherein the capsules comprise at least about 95% by weight of the water insoluble hair dye compound, on an anhydrous basis.

33. The method of claim 27 wherein the shell material further comprises a crosslinking agent.

34. The method of claim 27 wherein the leave-on composition includes about 0.1% to about 1% by weight of the suspending agent.

35. The method of claim 27 wherein the leave-on composition has a viscosity of about 50,000 to bout 100,000 centipoises.

* * * * *